United States Patent
Shah

(10) Patent No.: US 9,072,302 B2
(45) Date of Patent: Jul. 7, 2015

(54) PESTICIDAL COMPOSITION CONTAINING LAMBDA CYHALOTHRIN AND DIAFENTHIURON

(71) Applicant: Deepak Pranjivandas Shah, Mumbai (IN)

(72) Inventor: Deepak Pranjivandas Shah, Mumbai (IN)

( * ) Notice: Subject to any disclaimer, the term of this patent is extended or adjusted under 35 U.S.C. 154(b) by 309 days.

(21) Appl. No.: 13/847,706

(22) Filed: Mar. 20, 2013

(65) Prior Publication Data

US 2013/0253054 A1     Sep. 26, 2013

(30) Foreign Application Priority Data

Mar. 21, 2012   (IN) .......................... 753/MUM/2012

(51) Int. Cl.
*A01N 53/00*     (2006.01)
*A01N 47/30*     (2006.01)

(52) U.S. Cl.
CPC ................ *A01N 53/00* (2013.01); *A01N 47/30* (2013.01)

(58) Field of Classification Search
CPC .... A01N 47/30; A01N 53/00; A01N 2300/00
See application file for complete search history.

(56) References Cited

FOREIGN PATENT DOCUMENTS

EP             736252 A2 * 10/1996

\* cited by examiner

*Primary Examiner* — Sreeni Padmanabhan
*Assistant Examiner* — Jody Karol
(74) *Attorney, Agent, or Firm* — Harris, Shelton, Hanover & Walsh; Susan B. Fentress

(57) ABSTRACT

The present invention relates to a composition comprising an effective amount of lambda cyhalothrin in the range of 0.5% to 12%; an effective amount of diafenthiuron in the range of 15% to 70% wherein the ratio of lambda cyhalothrin to diafenthiuron is in the range of 1:4 to 1:35; and at least one agrochemical excipient.

6 Claims, No Drawings

PESTICIDAL COMPOSITION CONTAINING LAMBDA CYHALOTHRIN AND DIAFENTHIURON

CROSS REFERENCE TO RELATED APPLICATIONS

This application is a nonprovisional application which claims foreign priority under 35 U.S.C. §119 to an Indian patent application 753/MUM/2012 filed Mar. 21, 2012 in India (hereby specially incorporated by reference).

FIELD OF THE INVENTION

The present invention relates to a composition comprising lambda cyhalothrin, diafenthiuron and at least one agrochemical excipient.

BACKGROUND

It is observed very often, that prolonged usage of pesticides leads to development of resistance by pests which make the pesticide ineffective. This results in application of pesticide compositions in higher doses which is detrimental to the environment.

A significant obstacle faced by the researchers in this technical field is regarding pesticide activity. For protection of crops it is vital that biological activity of the pesticides should be improved and also that the activity should be persistent over a period of time.

Hence, there is a need to develop a composition which addresses the problem of resistance and soil toxicity and also is used at reduced dosages, controls environmental damage, offers broader crop protection spectrum, improved and healthy foliage, rainfastedness, improved crop yield, saves labour and control against various insects and pests, improves plant growth and is yet cost-effective to the end user.

Prior art patent application EP0736252 states the combinations of diafenthiuron with other insecticides. The patent application EP '252 teaches the list of several insecticides that can be used in combination with diafenthiuron. However it does not teach or provide the particular combination of diafenthiuron and lambdacyhalothrin nor does it disclose the concentration ranges and the ratios of diafenthiuron and lambda which shows synergistic effect and which does not lead to high loading of the harmful pesticides.

An insecticidal composition must satisfy a range of requirements to be viable on the market. One such requirement of the pesticidal composition is the ability to be selective in biologic action and have low toxicity and a high margin of safety to humans, crops, economic animals, aquatic organisms and birds. Another requirement is the desire that the composition should be environmental-friendly in that there should be demonstrably low impacts on the environment. Further, there should be none or little insect resistance to such compounds or combinations.

In a view of afore mentioned there is a need of preparing synergistic pesticidal composition comprising an effective amount of lambda cyhalothrin and an effective amount of diafenthiuron which provides improved efficacies at lower concentration compared to that observed with the individual components.

SUMMARY OF INVENTION

It has now been determined that a pesticidal composition comprising an effective amount of lambda cyhalothrin in the range of 0.5% to 12%; an effective amount of diafenthiuron in the range of 15% to 70% wherein ratio of lambda cyhalothrin to diafenthiuron is in the range of 1:4 to 1:35; and at least one agrochemical excipient has unexpectedly high activities in the control of various pests and insects for eg. white flies, affids, lepidoptera, jassids etc.

The pesticidal compositions offer a broad spectrum of protection, demonstrate synergistic effect against various pests, addresses the concerns of resistance, improve foliage, improve rainfastness and in various instances, improve crop yield and grain quality. The compositions disclosed herein, also serve as an intervention application between very specific actives, which alone are likely to lead to resistance in areas of epidemic and high frequency of pesticidal application.

It has also been found that the compositions of the present invention show markedly enhanced action against pests compared to the control rates that are obtained with the individual compounds.

DETAILED DESCRIPTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The present invention relates to a pesticidal composition comprising an effective amount of lambda cyhalothrin in the range of 0.5% to 12%; an effective amount of diafenthiuron in the range of 15% to 70% wherein the ratio of lambda cyhalothrin to diafenthiuron is in the range of 1:4 to 1:30; and further comprising at least one agrochemical excipient.

According to an embodiment, the ratio of the ratio of lambda cyhalothrin to diafenthiuron is in the range of 1:4 to 1:30. According to another embodiment, the ratio of lambda cyhalothrin to diafenthiuron is in the range of 1:7 to 1:16.

According to an embodiment, the composition may be in the form of emulsion concentrates (EC), wettable powders (WP), suspoemulsions (SE), microemulsions, capsulated suspension (CS), water dispersible granules (WG or WDG), ZC composition, ZC composition in WDG, pellets, seed dressings or emulsions for seed treatment, broadcast granules, gel, emulsions in water or oil dispersions. Preferably the composition is in the form of water dispersible granular composition or a ZC composition. A ZC composition is a combination of a capsulated suspension and a suspension concentrate.

Water dispersible granules can be defined as a pesticide formulation consisting of granules to be applied after disintegration and dispersion in water. As described herein, "WG" or "WDG" refer to water dispersible granules.

As defined herein, WP refers to a wettable powder, which can be a powder formulation to be applied as a suspension after dispersion in water. As defined herein, EC refers to an emulsifiable concentrate, which can be a liquid homogenous formulation to be applied as an emulsion after dilution in water. As described herein, ZC refers to a stable suspension of capsules and active ingredient, in fluid, normally intended for dilution with water before use. As described herein, CS refers to capsulated suspension which is a stable suspension of micro-encapsulated active ingredient in an aqueous continuous phase, intended for dilution with water before use. As described herein, SE refers to Suspo Emulsion, which is a fluid heterogenous formulation consisting of active ingredients in the form of solid particles and fine globules in continuous water phase.

According to an embodiment, the agrochemical excipient can include one or more of binders, surfactants, wetting and dispersing agents, emulsifiers, diluents, etc.

According to an embodiment, the composition is a water dispersible granular composition comprising an effective amount of lambda cyhalothrin; an effective amount of diafenthiuron; an inert filler having an absorbency capacity of 20% to 100% of its weight, and at least one agrochemical excipient.

According to an embodiment, at least one agrochemically acceptable excipient comprises wetting agents, dispersing agents, emulsifiers, binding agents, sticking agents, fillers, diluents, solvents, coating agents, stabilizers, chelating agents and coloring agents and buffering agent. However, those skilled in the art will appreciate that it is possible to utilize additional agrochemically acceptable excipients without departing from the scope of the present invention. The agrochemically acceptable excipient can be in the range from 4% to 60% of the total weight of the composition.

According to another embodiment, the inert filler which can be used has an absorbency capacity of 20 gm of oil per 100 gm of filler to 400 gm of oil/100 gm of filler.

According to yet another embodiment, the inert filler may include mineral earths and clays such as bentonite, perlite, talc, kaolin, sodium potassium, precipitated silica, precipitated silicates, aluminium silicate, diatomaceous earth, attapulgite, barium sulfate, mica, zeolites, calcium carbonate, etc. or a combination thereof.

According to another embodiment, surfactants which can be used as wetting agents and/or dispersing agents include sulfosuccinates, naphthalene sulfonates, sulfated esters, phosphate esters, sulfated alcohol, alkyl benzene sulfonates polycarboxylates, naphthalene sulfonate condensates, phenol sulfonic acid condensates, lignosulfonates, methyl oleyl taurates and polyvinyl alcohols. However, those skilled in the art will appreciate that it is possible to utilize other surfactants known in the art without departing from the scope of the invention.

According to another embodiment, the pesticidal composition is in the form of WDG composition comprising an effective amount of lambda cyhalothrin in the range of 0.5% to 12%; an effective amount of diafenthiuron in the range of 15% to 70% wherein the ratio of lambda cyhalothrin to diafenthiuron is in the range of 1:4 to 1:30; and further comprising at least one agrochemical excipient.

According to yet another embodiment, the pesticidal composition is in the form of ZC composition comprising an effective amount of lambda cyhalothrin in the range of 0.5% to 12%; an effective amount of diafenthiuron in the range of 15% to 70% wherein the ratio of lambda cyhalothrin to diafenthiuron is in the range of 1:4 to 1:30; and further comprising at least one agrochemical excipient.

The pesticidal composition may optionally further comprise antifoaming agents, stabilizers, buffering agents, chelating agents and coloring agents.

According to an embodiment, the composition comprising Lambda cyhalothrin and diafenthiuron can be prepared by various processes.

For instance water dispersible granular compositions can be obtained by preparing suspension or dispersion of diafenthiuron in a requisite amount of additives such as wetting agents, dispersing agents, emulsifiers and fillers. Further preparing a filler base of at least one sorptive filler and other additives; and blending the suspension or dispersion of diafenthiuron with the filler base to get a wet mass. The wet mass is then extruded and dried to get water dispersible granules of diafenthiuron (Step 1). Further the lambdacyhalothrin is formulated in a emulsifiable solution in a requisite amount of additives such as dispersing agents, emulsifiers etc. (Step 2). The emulsifiable solution obtained step 1 is then absorbed on the water dispersible granules of diafenthiuron obtained in step 1 to get the water dispersible granules of lambdacyhalothrin and diafenthiuron in combination.

Alternately, wettable powder compositions of lambdacyhalothrin and diafenthiuron can be prepared by first blending requisite amount of lambdacyhalothrin and the respective amount of diafenthiuron and the required additives such as wetting agents, dispersing agents and fillers. The mixture is then micronised using a suitable mill like fluid energy mill; to an average particle size of less than 50 microns, preferably less than 15 microns, preferably 4 to 6 microns to get the WP formulation comprising lambdacyhalothrin and diafenthiuron in combination.

Alternately ZC compositions of lambda cyhalothrin and diafenthiuron may be prepared as follows. Suspension concentrate (SC) compositions of diafenthiuron is prepared by milling a requisite amount of diafenthiuron technical in a dispersion of requisite amounts of surfactants and filler in a required quantity of water containing the anti freezing agent and having an average particle size of less than 2 microns (step 1). A Capsulated suspension (CS) formulation is prepared separately by first dispersing the solution of requisite quantity of lambda cyhalothrin, the monomer and the polymeric surfactant in solvent in a dispersion of nonionic emulsifier in water. After pH adjustment the dispersion is kept under stirring at 50 degree C. for about two hours and finally the dispersion is neutralised to get the CS of lambda cyhalothrin (Step 2). Finally the SC of diafenthiuron obtained in Step 1, the CS obtained in Step 2 and the requisite amount of Xanthum gel are mixed to get the ZC formulation of lambda cyhalothrin and diafenthiuron. To prepare ZC composition in WDG form SC of diafenthiuron (step 1), CS of lambda cyhalothrin (Step 2), suitable fillers and other additives were mixed and then dried by any of the appropriate drying method such as spray drying, fluidized bed spray drying, fluid bed spray granulator etc.

According to a still further embodiment, the invention further relates to a method of application of the agricultural composition to crops and plants.

Surprisingly, in particular, it has now been observed that, the pesticidal activity of the composition comprising lambda cyhalothrin in the range of 0.5% to 10% of the total composition, diafenthiuron in the range of 15% to 70% of the total composition wherein the ratio of lambda cyhalothrin to diafenthiuron is in the range of 1:4 to 1:30 and at least one agrochemically acceptable excipient, compared with the pesticidal activity of individual components, is not merely a combination of these actives, but also provides excellent synergistic effect.

The rates of application of the lambda cyhalothrin to diafenthiuron are reduced while retaining an equally good action. Further, the combined mixture also achieves a high degree of pest control where both individual substances have become completely ineffective when excessively low rates are applied. This allows a considerable widening of the spectrum of pests which can be controlled and, on the other hand, an increased safety upon use. In addition to the actual synergistic action with regard to the pesticidal activity, the compositions according to the invention additionally have other surprising advantages, which can also be termed synergistic in a wider sense: for example, they allow the control of pests which are not, or not sufficiently, controlled by the individual compounds, and the compositions according to the invention are better tolerated by plants, i.e. they are less phytotoxic than the individual compounds.

With the use of the agrochemical composition the number of applications to control wide range of pests appearing at the same time is minimized, which decreases labour costs. The composition is highly safe to the user and to the environment. The composition offers the user a single homogenous application eliminating the need for tank mix. The composition also is cost-effective, as it provides much greater simultaneous control and can be used in a variety of crops with a broader spectrum of protection. Also, the composition can serve as an intervention application between very specific actives which are likely to lead to resistance in areas of epidemic and high frequency of pesticidal applications.

The various advantageous properties associated with the compositions according to the invention, include but are not limited to: a broadening of the spectrum of pesticidal activity to other pests, for example to resistant strains; adequate control of the pests at a rate of application at which the individual compounds are not very effective, advantageous behaviour during formulating and/or upon application, improved stability, improved toxicological and/or ecotoxicological behaviour, improved crop characteristics including crop yields, and other advantages familiar to a person skilled in the art.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

The following examples will serve to illustrate the invention, but should not be construed as limiting the invention. All parts, percentages, ratios and the like in these examples and in the remainder of the specification and claims are in weight/weight percentages of the total composition unless otherwise indicated.

EXAMPLES OF THE COMPOSITIONS

Example 1

Lambda cyhalothrin 3%+Diafenthiuron 30% WG Formulations

Lambda cyhalothrin technical—3.4%
Diafenthiuron—31.7%
Naphthalene sulfonate—1.5%
Naphthalene sulfonate condensate—8.0%
Lignin sulfonate—8.0%
Perlite—25.0%
Mica—11.0%
N,N-dimethyl decanamide—4.0%
Ethoxylated tristeryl phenol—7.6%

Example 2

Lambda cyhalothrin 0.5%+Diafenthiuron 15% ZC Formulations

Lambda cyhalothrin tech—0.55%
Diafenthiuron tech—15.80%
Solvent C-9—0.20%
Atlox 4912—0.05%
Polyethylene glycol—4.00%
Atlas G5000—0.05%
Butylated UF resin—0.02%
Alkyl naphthalene sulfonate condensates—5.0%
Alkyl naphthalene sulfonate—1.00%
Xanthan gum—0.20%
Proxel GXL—0.20%
Water—72.93%

Example 3

Lambda cyhalothrin 1%+Diafenthiuron 50% WP Formulations

Lambda cyhalothrin tech—1.1%
Diafenthiuron tech—53.0%
Alkyl naphthalene sulfonate condensates—5.0%
Alkyl sulfosuccinate—1.0%
Lignin sulfonate—4.0%
Precipitated silica—5.0%
Kaolin—30.9%

Standards Used for Comparison:
Lambdacyhalothrin 5% EC (Sample D+L-17)
Diafenthiuron 50% WP (Sample D+L-18)
Samples for Comparison:
Prior Art Sample 1: (Example F8 of EP Patent '252):
Extruder granules comprising Mixture of active ingredients (2:1) 10%
Lambda cyhalothrin tech—3.34%
Diafenthiuron tech—6.64%
Sodium lignosulfonate 2%
Carboxymethylcellulose 1%
Kaolin 87%
The active ingredients are mixed with the additives, and the mixture is ground and moistened with water. This mixture is extruded, granulated and subsequently dried in a stream of air.
Prior Art Sample 2: (Example F10 of EP Patent '252)
Suspension Concentrate comprising Mixture of active ingredients (1:1)—40%
Lambda cyhalothrin tech—20%
Diafenthiuron tech—20%
Ethylene glycol—10%
Nonyl phenol polyethylene glycol ether—6%
Sodium lignosulfonate 10%
Carboxymethylcellulose—1%
70% aqueous formaldehyde solution—87%
Silicon oil in the form of a 75% aqueous emulsion—0.8%
The active ingredients are mixed with the additives, and the mixture is ground and moistened with water. This mixture is extruded, granulated and subsequently dried in a stream of air.
Prior Art Sample 3:
Emulsion concentrate comprising Mixture of active ingredients (1:100)
Lambda cyhalothrin tech—0.009%
Diafenthiuron tech—0.9%
Blend of nonyl phenol ethoxylate &
Calcium alkyl benzene sulfonate: 5.0
Solvent C-9: q.s
Prior Art Sample 4:
Wettable Powder comprising Mixture of active ingredients (1:50)
Lambda cyhalothrin tech—1.0%
Diafenthiuron tech—50.0%
Alkyl naphthalene sulfonate—2.0%
Alkyl naphthalene sulfonate condensate—8.0%
Precipitated silica—2.0%
Kaolin—q.s Efficacy Trials:

The efficacy trials conducted using stand-alone treatments of lambda cyhalothrin and diafenthiuron were done in accordance with standard recommended dosages for these active ingredients in India. However, it may be noted that the recommended dosages for each active ingredient may vary as per recommendations in a particular country, soil conditions, the nature of cultivars weather conditions and disease intensity.

Experimental Data:

In a field experiment the synergistic insecticidal effects of combination of Lambdacyhalothrin and Diafenthiuron at different concentration ranges was evaluated in controlling White fly, Affid, Lepidoptera and Jassid population on Brinja.

The synergistic insecticidal effects of combination were evaluated in comparison to the Lambda cyhalothrin 5% EC and Diafenthiuron 50% WP when used alone and also in comparison with the prior art sample 1, 2, 3 and 4 which were prepared as per prior art patent application EP '252.

The insecticide compositions were sprayed on five randomly selected plants. These plants were marked and the same were used throughout the treatment for calculating the number of white flies, Affid, Lepidoptera, and Jassid.

In this evaluation, percent inhibition of White fly, Affid, Lepidoptera, and Jassid population in the Brinjal crop was determined by counting the number of white flies, Affid, Lepidoptera and Jassid on the 3rd, 6th, 9th and 12th day after treatment with insecticidal composition. The count was conducted before and after spraying the insecticides and percent inhibition was based on these counts. Further, the synergistic effects of the insecticides were computed using Colby's method.

Details of Experiment:
  Design:
  Randomized Block Design (RBD)
  No. of replication: Two
  Plot size: 5 m×5 m=25 sq·m
  Treatment Details:
    As described herein, the abbreviation "DAT" refers to Days After Treatment; the abbreviation "DBT" refers to Days Before Treatment, the abbreviation "Y" refers that the synergy is observed and "N" refers that the synergy is not observed.

The treatments applied were as indicated in the table below:

TABLE 1

Samples of compositions comprising combination of lambda cyhalothrin and diafenthiuron and their dosages used for the trials

| Sample Code | Lambda cyhalothrin % | Diafenthiuron % | Formulation type | Dosage g/ha | Dosage g/25 Sq. meter | Lambda cyhalothrin g/ha | Diafenthiuron g/ha | Ratio of Lambda cyhalothrin:Diafenthiuron |
|---|---|---|---|---|---|---|---|---|
| D + L: 1 | 2 | 60 | WG | 800 | 2 | 16 | 480 | 1:30 |
| D + L: 2 | 2 | 50 | WG | 750 | 1.875 | 15 | 375 | 1:25 |
| D + L: 3 | 4 | 60 | WG | 500 | 1.25 | 20 | 300 | 1:15 |
| D + L: 4 | 2.5 | 40 | WG | 1000 | 2.5 | 25 | 400 | 1:16 |
| D + L: 5 | 3 | 40 | WG | 800 | 2 | 24 | 320 | 1:13.3 |
| D + L: 6 | 2.5 | 30 | WG | 900 | 2.25 | 22.5 | 270 | 1:12 |
| D + L: 7 | 3.5 | 35 | WG | 600 | 1.5 | 21 | 210 | 1:10 |
| D + L: 8 | 7.5 | 37.5 | WG | 400 | 1 | 30 | 150 | 1:5 |
| D + L: 9 | 0.5 | 15 | ZC | 2400 | 6 | 12 | 360 | 1:30 |
| D + L: 10 | 1.25 | 17.5 | ZC | 1800 | 4.5 | 22.5 | 315 | 1:14 |
| D + L: 11 | 2.5 | 27.5 | ZC | 940 | 2.35 | 23.5 | 258.5 | 1:11 |
| D + L: 12 | 1.75 | 17.5 | ZC | 1500 | 3.75 | 26.25 | 262.5 | 1:10 |
| D + L: 13 | 2.5 | 17.5 | ZC | 1000 | 2.5 | 25 | 175 | 1:7 |
| D + L: 14 | 10 | 45 | WDG | 300 | 0.75 | 30 | 135 | 1:4.5 |
| D + L: 15 | 2 | 70 | WDG | 750 | 1.875 | 15 | 525 | 1:35 |
| D + L: 16 | 12 | 48 | WDG | 275 | 0.6875 | 33 | 132 | 1:5 |
| D + L: 17 | 5 | 0 | EC | 500 | 1.25 | 25 | 0 | NA |
| D + L: 18 | 0 | 50 | WP | 800 | 2 | 0 | 400 | NA |
| Prior art sample 1 | 3.34 | 6.67 | Extruded granules | 600 | 1.5 | 20.04 | 40.02 | 1:2 |
| Prior art sample 2 | 10 | 10 | SC | 400 | 1 | 40 | 40 | 1:1 |
| Prior art sample 3 | 0.009 | 0.9 | EC | 5000 | 12.5 | 0.45 | 45 | 1:100 |
| Prior art sample 4 | 1 | 50 | WP | 1500 | 3.75 | 15 | 750 | 1:50 |

TABLE 2

Trial data showing the number of white fly before spraying insecticide compositions and that after 3rd, 6th, 9th and 12th day of the treatment

| Sample Code | Lambda cyhalothrin g/ha | Diafenthuron g/ha | White fly | | | | |
| | | | 1DBT | 3DAT | 6DAT | 9DAT | 12DAT |
|---|---|---|---|---|---|---|---|
| D + L: 1 | 16 | 480 | 40 | 13 | 5 | 2 | 2 |
| D + L: 2 | 15 | 375 | 30 | 7 | 5 | 2 | 0 |
| D + L: 3 | 20 | 300 | 45 | 10 | 3 | 3 | 0 |
| D + L: 4 | 25 | 400 | 20 | 4 | 0 | 0 | 1 |

TABLE 2-continued

Trial data showing the number of white fly before spraying insecticide compositions and that after 3rd, 6th, 9th and 12th day of the treatment

| Sample Code | Lambda cyhalothrin g/ha | Diafenthuron g/ha | 1DBT | 3DAT | 6DAT | 9DAT | 12DAT |
|---|---|---|---|---|---|---|---|
| D + L: 5 | 24 | 320 | 50 | 11 | 3 | 0 | 0 |
| D + L: 6 | 22.5 | 270 | 100 | 22 | 7 | 0 | 0 |
| D + L: 7 | 21 | 210 | 40 | 9 | 4 | 0 | 0 |
| D + L: 8 | 30 | 140 | 20 | 8 | 2 | 0 | 0 |
| D + L: 9 | 12 | 360 | 35 | 8 | 3 | 0 | 0 |
| D + L: 10 | 22.5 | 315 | 50 | 12 | 5 | 0 | 0 |
| D + L: 11 | 23.5 | 258.5 | 40 | 11 | 3 | 0 | 0 |
| D + L: 12 | 26.25 | 243.75 | 60 | 15 | 5 | 0 | 0 |
| D + L: 13 | 25 | 175 | 50 | 14 | 8 | 0 | 0 |
| D + L: 14 | 30 | 135 | 60 | 14 | 10 | 3 | 1 |
| D + L: 15 | 15 | 525 | 45 | 10 | 4 | 0 | 0 |
| D + L: 16 | 33 | 132 | 30 | 8 | 5 | 1 | 1 |
| D + L: 17 | 25 | 0 | 40 | 22 | 15 | 2 | 7 |
| D + L: 18 | 0 | 400 | 30 | 13 | 8 | 0 | 3 |
| Prior art sample 1 | | 40.02 | 45 | 35 | 20 | 15 | 15 |
| Prior art sample 2 | 40 | 40 | 50 | 30 | 27 | 25 | 19 |
| Prior art sample 3 | 0.45 | 45 | 30 | 30 | 28 | 33 | 30 |
| Prior art sample 4 | 15 | 750 | 50 | 23 | 10 | 0 | 8 |
| Control | 0 | 0 | 46 | 49 | 53 | 49 | 47 |

TABLE 3

Calculation of expected growth inhibition of white fly by Colby's method for combination of Lambda- cyhalothrin and diafenthiuron

| | white fly | | 3 DAT | 6 DAT | 9 DAT | 12DAT |
|---|---|---|---|---|---|---|
| X % inhibition | Lambda cyhalothrin (25 g/ha) | | 45 | 62.5 | 95 | 82.5 |
| X1 % Control | X1 = % Control (100 − X) | | 55 | 37.5 | 5 | 17.5 |
| Y % inhibition | Diafenthiuron (400 g/ha) | | 56.667 | 73.33 | 100 | 90 |
| Y1 % Control | Y1 = % Control (100 − Y) | | 43.333 | 26.67 | 0 | 10 |
| | X1 Y1 | | 2383.3 | 1000 | 0 | 175 |
| Expected Growth Control E1 | X1 Y1/100 | | 23.833 | 10 | 0 | 1.75 |
| Expected Growth Inhibition E | Expected Growth Inhibition (E = 100 − E1) | | 76.18 | 90 | 100 | 98.25 |

TABLE 4

Synergistic effect of combination of Lambdacyhalothrin and diafenthiuron on white fly

| White Fly | Samples | Ratio of Lambda cyhalothrin:Diafenthiuron | Lamda cyhalothrin g/ha | Diafenthiuron g/ha | 3DAS | 6DAS | 9DAS | 12DAS | Synergy |
|---|---|---|---|---|---|---|---|---|---|
| | | NA | 25 | 400 | 76.17 | 90 | 100 | 98.25 | |
| Observed Growth Inhibition | D + L-3 | 1:15 | 20 | 300 | 77.78 | 93.33 | 93.33 | 100 | YYYY |
| | D + L-4 | 1:16 | 25 | 400 | 80 | 100 | 100 | 100 | YYYY |
| | D + L-5 | 1:13.3 | 24 | 320 | 78 | 94 | 100 | 100 | YYYY |
| | D + L-6 | 1:12 | 22.5 | 270 | 78 | 93 | 100 | 100 | YYYY |
| | D + L-7 | 1:10 | 21 | 210 | 77.5 | 90 | 100 | 100 | YYYY |
| | D + L-9 | 1:30 | 12 | 360 | 77.14 | 91.43 | 100 | 100 | YYYY |
| | D + L-10 | 1:14 | 22.5 | 315 | 76 | 90 | 100 | 100 | YYYY |
| | D + L-11 | 1:11 | 23.5 | 259 | 72.5 | 92.5 | 100 | 100 | YYYY |
| | D + L-12 | 1:10 | 26.25 | 244 | 75 | 91.67 | 100 | 100 | YYYY |
| | D + L-13 | 1:7 | 25 | 175 | 72 | 84 | 100 | 100 | YYYY |
| | D + L-15 | 1:35 | 15 | 525 | 77.78 | 91.11 | 100 | 100 | YYYY |
| | Prior art Sample 1 | 1:2 | 20.04 | 40.02 | 22.22 | 55.56 | 66.67 | 66.67 | NNNN |

TABLE 4-continued

Synergistic effect of combination of Lambdacyhalothrin and diafenthiuron on white fly

| White Fly | Samples | Ratio of Lambda cyhalothrin:Diafenthiuron | Lamda cyhalothrin g/ha | Diafenthiuron g/ha | 3DAS | 6DAS | 9DAS | 12DAS | |
|---|---|---|---|---|---|---|---|---|---|
| | | | | Expected growth inhibition Calculated by Colby's method (Table 3) | | | | | |
| | | NA | 25 | 400 | 76.17 | 90 | 100 | 98.25 | Synergy |
| | Prior art Sample 2 | 1:1 | 40 | 40 | 40 | 46 | 50 | 62 | NNNN |
| | Prior art Sample 3 | 1:100 | 0.45 | 45 | 0 | 6.67 | −10 | 0 | NNNN |
| | Prior art Sample 4 | 1:50 | 15 | 750 | 54 | 80 | 100 | 84 | NNYN |

As shown in the above table, the values of observed growth inhibition have exceeded the values of expected growth inhibition calculated by colby's method. Hence it can be concluded, that Lambda cyhalothrin and Diafenthiuron when used in combination at lower concentration as compared to Lambda cyhalothrin (25 g/ha) and Diafenthiuron (400 g/ha) used independently at considerably higher concentrations, it shows synergism to considerable extent against white fly population and provides a better control. It was also observed that the samples which are prepared as per prior art composition (prior art sample 1, 2, 3 and 4) do not provide synergistic effect as observed for the compositions which are prepared as per the embodiments of the present invention.

TABLE 5

Below is the table showing the number of affids before spraying insecticide compositions and that after $3^{rd}$, $6^{th}$, $9^{th}$ and $12^{th}$ day of the treatment

| Sample Code | Lambda cyhalothrin g/ha | Diafenthuron g/ha | Affid | | | | |
|---|---|---|---|---|---|---|---|
| | | | 1DBT | 3DAT | 6DAT | 9DAT | 12DAT |
| D + L: 1 | 16 | 480 | 8 | 2 | 1 | 1 | 1 |
| D + L: 2 | 15 | 375 | 9 | 2 | 1 | 2 | 1 |
| D + L: 3 | 20 | 300 | 7 | 2 | 1 | 1 | 1 |
| D + L: 4 | 25 | 400 | 6 | 2 | 1 | 2 | 1 |
| D + L: 5 | 24 | 320 | 10 | 2 | 1 | 1 | 2 |
| D + L: 6 | 22.5 | 270 | 5 | 1 | 0 | 2 | 1 |
| D + L: 7 | 21 | 210 | 9 | 2 | 0 | 2 | 2 |
| D + L: 8 | 30 | 140 | 22 | 7 | 2 | 2 | 2 |
| D + L: 9 | 12 | 360 | 11 | 2 | 1 | 3 | 1 |
| D + L: 10 | 22.5 | 315 | 10 | 2 | 1 | 5 | 2 |
| D + L: 11 | 23.5 | 258.5 | 9 | 2 | 1 | 4 | 3 |
| D + L: 12 | 26.25 | 243.75 | 7 | 1 | 0 | 4 | 3 |
| D + L: 13 | 25 | 175 | 4 | 2 | 1 | 5 | 3 |
| D + L: 14 | 30 | 135 | 12 | 5 | 3 | 2 | 2 |
| D + L: 15 | 15 | 525 | 17 | 4 | 2 | 2 | 1 |
| D + L: 16 | 33 | 132 | 5 | 2 | 2 | 1 | 1 |
| D + L: 17 | 25 | 0 | 8 | 4 | 2 | 3 | 3 |
| D + L: 18 | 0 | 400 | 2 | 1 | 1 | 4 | 5 |
| Prior art sample 1 | 20.04 | 40.02 | 9 | 3 | 1 | 8 | 7 |
| Prior art sample 2 | 40 | 40 | 2 | 0 | 1 | 8 | 6 |
| Prior art sample 3 | 66.8 | 133.4 | 9 | 22 | 15 | 5 | 5 |
| Prior art sample 4 | 15 | 750 | 6 | 23 | 10 | 0 | 6 |
| Control | 0 | 0 | 5 | 4 | 8 | 19 | 21 |

TABLE 6

Calculation of expected growth inhibition of affid by Colby's method for combination of Lambda- cyhalothrin and diafenthiuron.

| | Affid | 3 DAT | 6 DAT | 9 DAT | 12DAT |
|---|---|---|---|---|---|
| X % inhibition | Lambda cyhalothrin (25 g/ha) | 50 | 75 | 62.5 | 62.5 |
| X1 = % Control (100 − X) | X1 = % Control (100 − X) | 50 | 25 | 37.5 | 37.5 |
| Y % inhibition | Diafenthiuron (400 g/ha) | 50 | 50 | −100 | −150 |

TABLE 6-continued

Calculation of expected growth inhibition of affid by Colby's
method for combination of Lambda- cyhalothrin and diafenthiuron.

| | Affid | 3 DAT | 6 DAT | 9 DAT | 12DAT |
|---|---|---|---|---|---|
| Y1 = % Control (100 − Y) | Y1 = % Control (100 − Y) | 50 | 50 | 200 | 250 |
| | X1 Y1 | 2500 | 1250 | 7500 | 9375 |
| Expected Growth Control E | X1 Y1/100 | 25 | 12.5 | 75 | 93.75 |
| Expected Growth Inhibition | Expected Growth Inhibition (E1 = 100 − E) | 75 | 87.5 | 25 | 6.25 |

TABLE 7

Synergistic effect of combination of Lambdacyhalothrin and diafenthiuron on Affid

| | | Ratio of Lambda cyhalothrin:Diafenthiuron | Lamda cyhalothrin g/ha | Diafenthiuron g/ha | 3DAS | 6DAS | 9DAS | 12DAS | |
|---|---|---|---|---|---|---|---|---|---|
| | | | Expected growth inhibition Calculated by Colby's method (Table 6) | | | | | | |
| Affid | Samples | NA | 25 | 400 | 75 | 87.5 | 25 | 6.25 | Synergy |
| Observed Growth Inhibition | D + L-1 | 1:30 | 60 | 480 | 75 | 87.5 | 87.5 | 87.5 | YYYY |
| | D + L-2 | 1:25 | 15 | 375 | 77.78 | 88.89 | 77.78 | 88.89 | YYYY |
| | D + L-5 | 01:13.3 | 24 | 320 | 80 | 90 | 90 | 80 | YYYY |
| | D + L-6 | 1:12 | 22.5 | 270 | 80 | 100 | 60 | 80 | YYYY |
| | D + L-7 | 1:10 | 21 | 210 | 77.78 | 100 | 77.78 | 77.78 | YYYY |
| | D + L-9 | 1:30 | 12 | 360 | 81.82 | 90.91 | 72.72 | 90.91 | YYYY |
| | D + L-10 | 1:14 | 25 | 750 | 80 | 90 | 50 | 80 | YYYY |
| | D + L-11 | 1:11 | 22.5 | 315 | 77.77 | 88.89 | 55.55 | 66.67 | YYYY |
| | D + L-12 | 1:10 | 23.5 | 258.5 | 85.71 | 100 | 42.86 | 57.14 | YYYY |
| | D + L-15 | 1:35 | 15 | 525 | 76.47 | 88.23 | 88.23 | 94.11 | YYYY |
| | Prior art Sample1 | 1:2 | 20.04 | 40.02 | 27.27 | 63.63 | 72.72 | 72.72 | NNYY |
| | Prior art Sample2 | 1:1 | 40 | 40 | 44.44 | 55.56 | 66.67 | 66.67 | NNYY |
| | Prior art Sample3 | 1:100 | 0.45 | 45 | 16.67 | 33.33 | 16.67 | 33.33 | NNNY |
| | Prior art Sample4 | 1:50 | 15 | 750 | 50 | 80 | 40 | 20 | NNYY |

As shown in the above table, the values of observed growth inhibition have exceeded the values of expected growth inhibition calculated by colby's method. Hence it can be concluded, that Lambda cyhalothrin and Diafenthiuron when used in combination at lower concentration as compared to Lambda cyhalothrin (25 g/ha) and Diafenthiuron (400 g/ha) used independently at considerably higher concentrations, it shows synergism to considerable extent against affid population and provides a better control. It was also observed that the samples which are prepared as per prior art composition (prior art sample 1, 2, 3 and 4) do not provide synergistic effect as observed for the compositions which are prepared as per the embodiments of the present invention.

TABLE 8

Below is the table showing the number of Lepidoptera before spraying insecticide compositions and that after 3$^{rd}$, 6$^{th}$ and 9$^{th}$ and 12$^{th}$ day of the treatment

| Sample Code | Lambda cyhalothrin g/ha | Diafenthiuron g/ha | Lepidoptera | | | | |
|---|---|---|---|---|---|---|---|
| | | | 1DBT | 3DAT | 6DAT | 9DAT | 12DAT |
| D + L: 1 | 16 | 480 | 13 | 5 | 2 | 0 | 1 |
| D + L: 2 | 15 | 375 | 12 | 2 | 1 | 0 | 1 |
| D + L: 3 | 20 | 300 | 3 | 1 | 1 | 0 | 0 |
| D + L: 4 | 25 | 400 | 7 | 2 | 1 | 0 | 0 |
| D + L: 5 | 24 | 320 | 9 | 3 | 1 | 0 | 0 |
| D + L: 6 | 22.5 | 270 | 4 | 2 | 0 | 0 | 1 |
| D + L: 7 | 21 | 210 | 5 | 2 | 1 | 0 | 1 |
| D + L: 8 | 30 | 140 | 9 | 3 | 1 | 0 | 0 |
| D + L: 9 | 12 | 360 | 11 | 3 | 0 | 0 | 0 |
| D + L: 10 | 22.5 | 315 | 8 | 2 | 0 | 0 | 0 |
| D + L: 11 | 23.5 | 258.5 | 13 | 3 | 0 | 0 | 0 |
| D + L: 12 | 26.25 | 243.75 | 9 | 2 | 1 | 0 | 0 |

TABLE 8-continued

Below is the table showing the number of Lepidoptera before spraying insecticide compositions and that after 3$^{rd}$, 6$^{th}$ and 9$^{th}$ and 12$^{th}$ day of the treatment

| Sample Code | Lambda cyhalothrin g/ha | Diafenthuron g/ha | 1DBT | 3DAT | 6DAT | 9DAT | 12DAT |
|---|---|---|---|---|---|---|---|
| D + L: 13 | 25 | 175 | 10 | 2 | 0 | 0 | 0 |
| D + L: 14 | 30 | 135 | 12 | 5 | 3 | 1 | 1 |
| D + L: 15 | 15 | 525 | 15 | 6 | 4 | 2 | 2 |
| D + L: 16 | 33 | 132 | 4 | 2 | 1 | 0 | 1 |
| D + L: 17 | 25 | 0 | 3 | 2 | 1 | 0 | 2 |
| D + L: 18 | 0 | 400 | 8 | 5 | 4 | 1 | 1 |
| Prior art sample 1 | 20.04 | 40.02 | 11 | 8 | 4 | 3 | 3 |
| Prior art sample 2 | 40 | 40 | 9 | 3 | 2 | 0 | 2 |
| Prior art sample 3 | 66.8 | 133.4 | 6 | 5 | 4 | 5 | 4 |
| Prior art sample 4 | 15 | 750 | 10 | 4 | 2 | 1 | 1 |
| Control | 0 | 0 | 5 | 4 | 8 | 19 | 21 |

TABLE 9

Calculation of expected growth inhibition of Lepidoptera by Colby's method for combination of Lambda- cyhalothrin and diafenthiuron

| | Lepidoptera | 3 DAT | 6 DAT | 9 DAT | 12DAT |
|---|---|---|---|---|---|
| X % inhibition | Lambda cyhalothrin (25 g/ha) | 33.333 | 66.667 | 100 | 33.33 |
| X1 = % Control (100 − X) | X1 = % Control (100 − X) | 66.667 | 33.333 | 0 | 66.67 |
| Y % inhibition | Diafenthiuron (400 g/ha) | 37.5 | 50 | 87.5 | 87.5 |
| Y1 = % Control (100 − Y) | Y1 = % Control (100 − Y) | 62.5 | 50 | 0 | 12.5 |
| | X1 Y1 | 4166.7 | 1666.7 | 0 | 833.3 |
| Expected Growth Control E | X1 Y1/100 | 41.667 | 16.667 | 0 | 8.333 |
| Expected Growth Inhibition | Expected Growth Inhibition (E1 = 100 − E) | 58.33 | 83.33 | 100 | 91.67 |

TABLE 10

Synergistic effect of combination of Lambdacyhalothrin and diafenthiuron on Lepidoptera

| Lepidoptera | Samples | Ratio of Lambda cyhalothrin:Diafenthiuron | Lamda cyhalothrin g/ha | Diafenthiuron g/ha | 3DAS | 6DAS | 9DAS | 12DAS | Synergy |
|---|---|---|---|---|---|---|---|---|---|
| | | Expected growth inhibition Calculated by Colby's method (Table 9) | | | | | | | |
| | | NA | 25 | 400 | 58.33 | 83.33 | 100 | 91.67 | |
| Observed Growth Inhibition | D + L-1 | 1:30 | 16 | 480 | 61.54 | 84.62 | 100 | 92.31 | YYYY |
| | D + L-2 | 1:25 | 15 | 375 | 83.33 | 91.67 | 100 | 91.67 | YYYY |
| | D + L-4 | 1:16 | 25 | 400 | 71.43 | 85.71 | 100 | 100 | YYYY |
| | D + L-5 | 1:13.3 | 24 | 320 | 66.67 | 88.89 | 100 | 100 | YYYY |
| | D + L-8 | 1:15 | 30 | 140 | 66.67 | 88.89 | 100 | 100 | YYYY |
| | D + L-9 | 1:30 | 12 | 360 | 72.73 | 100 | 100 | 100 | YYYY |
| | D + L-10 | 1:14 | 25 | 750 | 87.5 | 87.5 | 100 | 100 | YYYY |
| | D + L-11 | 1:11 | 22.5 | 315 | 84.62 | 100 | 100 | 100 | YYYY |
| | D + L-12 | 1:10 | 23.5 | 258.5 | 66.67 | 100 | 100 | 100 | YYYY |
| | D + L-13 | 1:7 | 26.25 | 243.75 | 80 | 90 | 100 | 100 | YYYY |
| | Prior art Sample 1 | 1:2 | 20.04 | 40.02 | 27.27 | 63.64 | 72.73 | 72.73 | NNNN |
| | Prior art Sample 2 | 1:1 | 40 | 40 | 66.67 | 77.78 | 100 | 77.78 | YNYN |
| | Prior art Sample 3 | 1:100 | 0.45 | 45 | 16.67 | 33.33 | 16.67 | 33.33 | NNNN |
| | Prior art Sample 4 | 1:50 | 15 | 750 | 60 | 80 | 90 | 90 | YNNN |

As shown in the above table, the values of observed growth inhibition have exceeded the values of expected growth inhibition calculated by colby's method. Hence it can be concluded, that Lambda cyhalothrin and Diafenthiuron when used in combination at lower concentration as compared to Lambda cyhalothrin (25 g/ha) and Diafenthiuron (400 g/ha) used independently at considerably higher concentrations, it shows synergism to considerable extent against Lepidoptera population and provides a better control. It was also observed that the samples which are prepared as per prior art composition (prior art sample 1, 2, 3 and 4) do not provide synergistic effect as observed for the compositions which are prepared as per the embodiments of the present invention.

TABLE 11

Below is the table showing the number of Jassid before spraying insecticide compositions and that after $3^{rd}$, $6^{th}$ and $9^{th}$ and $12^{th}$ day of the treatment

| Sample Code | Lambda cyhalothrin g/ha | Diafenthiuron g/ha | Jassid | | | | |
|---|---|---|---|---|---|---|---|
| | | | 1DBT | 3DAT | 6DAT | 9DAT | 12DAT |
| D + L: 1 | 16 | 480 | 5 | 4 | 2 | 1 | 0 |
| D + L: 2 | 15 | 375 | 3 | 2 | 1 | 0 | 0 |
| D + L: 3 | 20 | 300 | 4 | 2 | 2 | 1 | 0 |
| D + L: 4 | 25 | 400 | 6 | 3 | 1 | 0 | 0 |
| D + L: 5 | 24 | 320 | 5 | 2 | 1 | 1 | 0 |
| D + L: 6 | 22.5 | 270 | 4 | 1 | 0 | 0 | 0 |
| D + L: 7 | 21 | 210 | 3 | 1 | 1 | 0 | 0 |
| D + L: 8 | 30 | 140 | 4 | 2 | 1 | 1 | 0 |
| D + L: 9 | 12 | 360 | 3 | 2 | 1 | 0 | 1 |
| D + L: 10 | 22.5 | 315 | 5 | 2 | 1 | 0 | 0 |
| D + L: 11 | 23.5 | 258.5 | 6 | 3 | 1 | 1 | 0 |
| D + L: 12 | 26.25 | 243.75 | 4 | 2 | 1 | 0 | 0 |
| D + L: 13 | 25 | 175 | 3 | 1 | 0 | 1 | 0 |
| D + L: 14 | 30 | 135 | 5 | 2 | 2 | 1 | 1 |
| D + L: 15 | 15 | 525 | 9 | 5 | 4 | 3 | 1 |
| D + L: 16 | 33 | 132 | 8 | 3 | 2 | 1 | 1 |
| D + L: 17 | 25 | 0 | 5 | 3 | 3 | 2 | 5 |
| D + L: 18 | 0 | 400 | 4 | 4 | 2 | 4 | 5 |
| Prior art sample 1 | 20.04 | 40.02 | 6 | 4 | 2 | 1 | 1 |
| Prior art sample 2 | 40 | 40 | 9 | 3 | 3 | 2 | 0 |
| Prior art sample 3 | 66.8 | 133.4 | 4 | 4 | 4 | 3 | 3 |
| Prior art sample 4 | 15 | 750 | 3 | 2 | 1 | 1 | 0 |
| Control | 0 | 0 | 5 | 4 | 1 | 19 | 21 |

TABLE 12

Calculation of expected growth inhibition of Jassid by Colby's method for combination of Lambda- cyhalothrin and diafenthiuron

| | Jassid | 3 DAT | 6 DAT | 9 DAT | 12DAT |
|---|---|---|---|---|---|
| X % inhibition | Lambda cyhalothrin (25 g/ha) | 40 | 40 | 60 | 0 |
| X1 = % Control (100 − X) | X1 = % Control (100 − X) | 60 | 60 | 40 | 100 |
| Y % inhibition | Diafenthiuron (400 g/ha) | 0 | 50 | 0 | −25 |
| Y1 = % Control (100 − Y) | Y1 = % Control (100 − Y) | 100 | 50 | 100 | 125 |
| | X1 Y1 | 6000 | 3000 | 4000 | 12500 |
| Expected Growth Control E | X1 Y1/100 | 60 | 30 | 40 | 125 |
| Expected Growth Inhibition | Expected Growth Inhibition (E1 = 100 − E) | 40 | 70 | 60 | −25 |

TABLE 13

Synergistic effect of combination of Lambdacyhalothrin and diafenthiuron on Jassid

| | | Ratio of Lambda cyhalothrin:Diafenthiuron | Lamda cyhalothrin g/ha | Diafenthiuron g/ha | 3DAS | 6DAS | 9DAS | 12DAS | |
|---|---|---|---|---|---|---|---|---|---|
| | | Expected growth inhibition Calculated by Colby's method (Table 12) | | | | | | | |
| Jassid | Samples | NA | 25 | 400 | 40 | 70 | 60 | −25 | Synergy |
| Observed | D + L-3 | 1:15 | 20 | 300 | 50 | 75 | 75 | 100 | YYYY |
| Growth | D + L-4 | 1:16 | 25 | 400 | 50 | 83.33 | 100 | 100 | YYYY |
| Inhibition | D + L-5 | 1:13.3 | 24 | 320 | 60 | 80 | 80 | 100 | YYYY |

TABLE 13-continued

Synergistic effect of combination of Lambdacyhalothrin and diafenthiuron on Jassid

| Jassid | Samples | Ratio of Lambda cyhalothrin:Diafenthiuron | Lamda cyhalothrin g/ha | Diafenthiuron g/ha | 3DAS | 6DAS | 9DAS | 12DAS | |
|---|---|---|---|---|---|---|---|---|---|
| | | | | Expected growth inhibition Calculated by Colby's method (Table 12) | | | | | |
| Jassid | | NA | 25 | 400 | 40 | 70 | 60 | −25 | Synergy |
| | D + L-6 | 1:12 | 22.5 | 270 | 75 | 100 | 100 | 100 | YYYY |
| | D + L-8 | 1:15 | 30 | 140 | 50 | 75 | 75 | 100 | YYYY |
| | D + L-10 | 1:14 | 25 | 750 | 60 | 80 | 100 | 100 | YYYY |
| | D + L-11 | 1:11 | 22.5 | 315 | 50 | 83.33 | 83.33 | 100 | YYYY |
| | D + L-12 | 1:10 | 23.5 | 258.5 | 50 | 75 | 100 | 100 | YYYY |
| | D + L-13 | 1:7 | 26.25 | 243.75 | 66.67 | 100 | 66.67 | 100 | YYYY |
| | D + L-14 | 1:4.5 | 30 | 135 | 60 | 60 | 80 | 80 | YYYY |
| | D + L-15 | 1:35 | 15 | 525 | 44.44 | 55.56 | 66.67 | 88.89 | YYYY |
| | D + L-16 | 1:4 | 33 | 132 | 62.5 | 75 | 87.5 | 87.5 | YYYY |
| | Prior art Sample 1 | 1:2 | 20.04 | 40.02 | 33.33 | 66.67 | 83.33 | 83.33 | NNYY |
| | Prior art Sample 2 | 1:1 | 40 | 40 | 66.67 | 66.67 | 77.78 | 100 | YNYY |
| | Prior art Sample 3 | 1:100 | 0.45 | 45 | 0 | 0 | 25 | 25 | NNNY |
| | Prior art Sample 4 | 1:50 | 15 | 750 | 33.33 | 66.67 | 66.67 | 100 | NNYY |

As shown in the above table, the values of observed growth inhibition have exceeded the values of expected growth inhibition calculated by colby's method. Hence it can be concluded, that Lambda cyhalothrin and Diafenthiuron when used in combination at lower concentration as compared to Lambda cyhalothrin (25 g/ha) and Diafenthiuron (400 g/ha) used independently at considerably higher concentrations, it shows synergism to considerable extent against Jassid population and provides a better control.

It was also observed that the samples which are prepared as per prior art composition (prior art sample 1, 2, 3 and 4) do not provide synergistic effect as observed for the compositions which are prepared as per the embodiments of the present invention.

It was observed that the combination of Lambda cyhalothrin and Diafenthiuron was more effective against white fly, affid, Lepidoptera and Jassid population as compared to lambda cyhalothrin and diafenthiuron used independently at considerably higher concentrations. It should be noted here that the insecticides used in the combination mixture showed higher effectiveness against the pest population at lower dosages and for a longer period of time, thus reducing the impact of bioaccumulation on the environment.

While the invention has been described with reference to specific embodiments, it will be appreciated that numerous variations, modifications and embodiments are possible, and accordingly all such variations, modifications and embodiments are to be regarded as deemed within the scope and spirit of the invention.

I claim:

1. A pesticidal composition comprising an effective amount of lambda cyhalothrin in the range of 0.5% to 12%; an effective amount of diafenthiuron in the range of 15% to 70% wherein the ratio of lambda cyhalothrin to diafenthiuron is in the range of 1:4 to 1:35; and at least one agrochemical excipient.

2. The pesticidal composition of claim 1, wherein the composition is in the form of emulsion concentrates, wettable powders, suspoemulsions, microemulsions, capsulated suspension, water dispersible granules, ZC composition, pellets, seed dressings or emulsions for seed treatment, broadcast granules, gel, emulsion in water or oil dispersions or combination thereof.

3. The pesticidal composition of claim 1, wherein the ratio of lambda cyhalothrin to diafenthiuron is in the range of 1:7 to 1:16 and at least one agrochemical excipient.

4. The pesticidal composition of claim 1, wherein the composition is in the form of water dispersible granular composition comprising an effective amount of lambda cyhalothrin; an effective amount of diafenthiuron; an inert filler having an absorbency capacity of 20% to 100% of its weight, and at least one agrochemical excipient.

5. The pesticidal composition of claim 1, wherein the composition is in the form of ZC composition comprising lambda cyhalothrin in the range of 0.5% to 12% and amount of diafenthiuron in the range of 15% to 70%; and at least one agrochemical excipient.

6. The pesticidal composition of claim 1, wherein the composition is in the form of WDG composition comprising lambda cyhalothrin in the range of 0.5% to 12% and amount of diafenthiuron in the range of 15% to 70%; and at least one agrochemical excipient.

* * * * *